United States Patent [19]

Lorenzoni et al.

[11] Patent Number: 5,068,429
[45] Date of Patent: * Nov. 26, 1991

[54] METHOD OF PURIFICATION OF THE OXALIC ACID DIAMIDE

[75] Inventors: Loreno Lorenzoni, Porto Torres; Nino Dessantis, Sassari; Angelo Virdis, Usini, all of Italy

[73] Assignee: Enichem Anic S.p.A., Palermo, Italy

[*] Notice: The portion of the term of this patent subsequent to Sep. 10, 2008 has been disclaimed.

[21] Appl. No.: 426,531

[22] Filed: Oct. 24, 1989

Related U.S. Application Data

[63] Continuation of Ser. No. 32,552, Apr. 1, 1987, abandoned.

[30] Foreign Application Priority Data

Apr. 17, 1986 [IT] Italy .................................. 20122 A86

[51] Int. Cl.⁵ ...................... C07B 63/00; C07C 103/14
[52] U.S. Cl. ..................................... 564/160; 564/125
[58] Field of Search ................ 564/160, 125, 206, 216

[56] References Cited

U.S. PATENT DOCUMENTS

| 3,776,957 | 12/1973 | Newkirk | 564/206 |
| 3,989,753 | 11/1976 | Riemenschneider et al. | 564/125 |

FOREIGN PATENT DOCUMENTS

| 2427269 | 6/1974 | Fed. Rep. of Germany | 564/160 |
| 2423538 | 11/1975 | Fed. Rep. of Germany | 564/160 |
| 38-9267 | 9/1970 | Japan | 564/206 |
| 51-29430 | 3/1976 | Japan | 564/125 |
| 59-36647 | 2/1984 | Japan | 564/160 |
| 59-39858 | 3/1984 | Japan | 564/160 |

*Primary Examiner*—Carolyn Elmore
*Attorney, Agent, or Firm*—Oblon, Spivak, McClelland, Maier & Neustadt

[57] ABSTRACT

A method of removing copper from oxamide obtained through a process which involves the use of copper catalysts, by contacting it with an aqueous solution of a suitable complexing agent, which is capable of forming copper-containing water-soluble complexes and imparts to the aqueous solution a pH comprised between 2 and 8, optionally repeating the contacting step and, finally, recovering the purified oxamide by solid-liquid separation techniques.

The claimed process affords oxamide containing less than 25 ppm of copper.

11 Claims, No Drawings

METHOD OF PURIFICATION OF THE OXALIC ACID DIAMIDE

This application is a continuation of application Ser. No. 032,552, filed on Apr. 1, 1987, now abandoned.

The present invention refers to a method of purification of the oxalic acid diamide obtained through a process which involves the use of copper catalysts.

The oxalic acid diamide, or oxamide, is a product which finds different applications in several chemical fields either as finished product or as an intermediate.

It is in fact commonly used in agriculture as a slow release fertilizer and a feed additive, in the plastics and dye sectors as a stabilizer, and as an intermediate for several different products such as, for instance, the corresponding diacetyl derivative employed in the detergency field.

Large-scale use of oxamide has become however economically feasible only in the last ten years owing to the introduction of the Hoechst process.

Up to that time, in fact, oxamide had been produced by oxidation of HCN with hydrogen peroxide or nitrogen dioxide.

Apart from the high cost of the oxidizing agents and the separation problems, in both cases it was necessary to carry out the synthesis in two separate steps, isolating first the intermediate cyanogen and hydrating then this intermediate to oxamide. All these drawbacks rendered the above synthesis unsuitable for industrial scale. On the contrary, the Hoechst process, that consists in the catalytic oxidation of HCN with air or oxygen using a solution of copper salts in acetic acid as the catalyst, allows the preparation of oxamide in a single step and with almost quantitative yields.

The Hoechst process, as well as all the improvements thereof which still make use of copper catalysts, however, has the disadvantage of providing oxamide containing from 500 to 1500 ppm of copper.

Besides giving an undesired color to the product, the presence of these amounts of copper renders the obtained oxamide unsuitable for some industrial use.

Copper contained in the oxamide prepared by this process however binds so tightly to the oxamide substrate or adheres so steadily to the surface of the oxamide, that repeated washings with water or other solvents do not afford its removal to a substantial extent.

One of the conventional methods tried to solve this problem, was crystallization.

However, besides considerably lowering the yields, this method proved to be rather unsuitable because of the poor solubility of oxamide in most organic solvents.

It has now surprisingly been found that it is possible to achieve an almost complete removal of copper from copper-containing oxamide by contacting this compound with an aqueous solution of a suitable complexing agent which is capable of forming copper-containing water-soluble complexes and imparts to the solution a pH comprised between 2 and 8.

More particularly, it has been found that a class of complexing agents particularly suitable for the purification method of the present invention, comprises those compounds which contain two or more carboxy groups, either free or partially salified with alkaline or alkaline-earth metals, linked to tertiary or secondary nitrogen atoms, such as, for instance, N,N'-1,2-ethandiylbis[N-(carboxymethyl)glycine] (EDTA), N,N-bis(-carboxymethyl)glycine (NTA), N,N-bis[2-[bis(carboxymethyl)amino]-ethyl]glycine (DTPA), N,N'-cyclohexandiylbis[N-(carboxymethyl)glycine] (DCTA), N,N'-(oxydi-2,1-ethandiyl)bis[N-(carboxymethyl)glycine] (EETA), N,N'-(thiodi-2,1-ethandiyl)-bis[N-(carboxymethyl)glycine] (DESTA), and the like compounds, as well as the corresponding derivatives partially salified with alkaline or alkaline-earth metals. The purification process of the present invention is simply carried out by contacting powdered oxamide, obtained through the so-called Hoechst process or any other similar process still involving the use of copper catalysts (see for instance Chem. Abst. 84 89647, 85 93873, 123382, and 123383, 101 25378, and 40215) with an aqueous solution of the complexing agent, according to any of the techniques commonly used for solid-liquid contacting.

Preferably, however, the dispersed contact method is used which involves motion of solid particles relative to each other and also relative to the aqueous solution. Agitation in fact permits thorough contacting of the solid with the aqueous solution and, accordingly, this method afforded optimum results in terms of reduced copper content of the purified oxamide. Prior treatment of the oxamide obtained by the Hoechst process or any improvement thereof, may be envisaged in order to make the solid particles more accessible to the aqueous solution. Said prior treatment may involve crushing, grinding, milling and the like operations. However too fine division may result in packing of solid during purification, thus preventing free flow of the aqueous solution through the solid particles. It has been found that, for a better contact, powdered oxamide, with a particle size comprised between 300 and 3000 mesh, is preferably used.

In the actual practice, the disperded contact is usually effected by charging the oxamide to be purified and the aqueous solution of the complexing agent in a suitable vessel, under stirring.

The aqueous solution typically contains the complexing agent in percentages, by weight, comprised between 0.01 and 10, and preferably between 0.2 and 6.

The amount of the suitably selected aqueous solution to be employed in the purification method of the present invention is such that the number of equivalents of the complexing agent is at least equal to, but preferably higher than, the number of equivalents of copper to be removed.

The purification may generally be carried out at a temperature comprised between 60° and 150° C. and preferably between 100° and 125° C., allowing oxamide to be purified and the aqueous solution of the complexing agent to be in contact for a period of time generally comprised between 1 and 6 hours. After this time, the temperature is brought to room temperature and the purified oxamide is separated from the solution of the complexing agent containing the removed copper, by means of the conventional techniques used for solid-liquid separations, such as filtration, decantation, or centrifugation.

If a thorough purification is desired, said procedure can be repeated once o more times using fresh solutions of the complexing agent.

Contacting can be carried out also in a multiple-contact system consisting of a number of batch contact units arranged in a line or a circle. The main feature of this multi-contact system is that solids remain in each unit agitated vessel but are subjects to multiple contacts with aqueous solutions of the complexing agent having a different extraction efficiency. More particularly, fresh aqueous solution and oxamide to be purified are contacted, under stirring, in the first stage. The aqueous solution is then transferred from vessel to vessel in a given order to treat progressively the less purified oxamide and leaves the system after contact with fresh oxamide. On the other hand, the final contact of most nearly purified oxamide is with a fresh solution of the complexing agent. A solution of the complexing agent can be used until, in the last step of the above multi-stage system, a critical concentration of copper is reached above which the extracting capacity of the solution is very low.

The exhausted aqueous solution can then be easily regenerated by means of suitable chemical treatments. It is possible in fact, for instance when the above cited polycarboxylic acids or their corresponding partially salified derivatives are ;employed as the complexing agents, to recover the complexing agent, e.g. by acidifying the exhausted solution thus causing the organic acid to precipitate, and recycle it with or without prior conversion into its alkaline or alkaline earth metal salt. It is also possible to separate from the exhausted solution the copper there contained, for instance, by precipitation as an insoluble copper salt.

The degree of purity of the oxamide obtainable by the purification process of the present invention depends on the solution of complexing agent employed, the ratio by weight between the complexing solution and oxamide, the temperature, the contacting time, and the number of contacting steps.

It is always possible, however, with a limited number of contacting steps (typically 2 or 3), to obtain oxamide containing less than 25 ppm of copper.

The oxamide recovered by filtration following the above treatment, generally corresponds to more than 98% of the starting oxamide, whereas the less than 2% left, is lost either through solubilization in the extracting solution or through undesired side-reactions in the purification environment.

This loss essentially depends on the temperature of the treatment, which affects both oxamide solubility in water and the rate of any side-reaction, and mainly on the pH of the solution.

According to a preferred embodiment of the present invention, in order to get the highest recovery yields, contacting of the oxamide to be purified with the aqueous solution of the complexing agent is carried out at a temperature comprised within the temperature range set forth above (from 60° to 150° C.), which substantially corresponds to the lowest temperature range which still allows the best copper-extracting efficiency, and a pH value comprised between 2 and 8. At a pH either lower than 2 or higher than 8, oxamide readily converts into several degradation products.

The following examples which illustrate in further detail the process of the present invention, particularly in its preferred embodiments, should not be considered anyway as a limitation to the scopes thereof.

EXAMPLE 1

A 5% solution of EDTA disodium salt in water (30 g) and oxamide to be purified (3 g) having an average particle size of about 1500 mesh, prepared by oxidizing HCN with oxygen in the presence of copper salts in $CH_3COOH/H_2O$ and containing 950 ppm of copper, are charged into a thermostatted autoclave equipped with a power-driven solids agitator. The mixture is heated to 100° C. and stirred at this temperature for 3 hours, then it is cooled to room temperature and the purified oxamide is separated from the liquid phase by centrifugation. Oxamide is then washed with water (20 ml) and centrifuged again, and the recovered oxamide is dried at 100° C. up to constant weight (2.9 g) (97% of the charged oxamide).

A small portion of the thus purified oxamide is dissolved in a mixture of sulphuric and nitric acids and analyzed by atomic absorption to determine the copper content which resulted to be 25 ppm.

Using the same equipment as above, the oxamide obtained by the above treatment is further purified by charging it (2 g) and a fresh 5% solution of EDTA disodium salt in water (20 ml) into the autoclave.

After heating the mixture to 100° C., under stirring, for 3 hours, the solid is separated, washed with water and separated again by centrifugation according to the above techniques.

Upon drying, 1.95 g of oxamide are recovered; atomic absorption analysis of a sample of the obtained product gives 15 ppm of copper.

With a third treatment, under the same conditions, carried out on 1.5 g of the oxamide obtained in the second purification step, 1.45 g of oxamide are recovered containing 9 ppm of copper.

EXAMPLE 2

An aqueous solution (30 ml) containing 270 ppm of EDTA and oxamide (3 g) to be purified, are charged into an autoclave as in example 1. The mixture is heated under stirring to 120° C. for 3 hours, and then it is cooled to room temperature. Upon centrifugation, washing with water (20 ml) and drying, 2.9 g of oxamide are recovered. Atomic absorption analysis of the thus purified oxamide, triturated with a mixture of sulphuric and nitric acids, reveals 70 ppm of copper.

EXAMPLE 3

An aqueous solution (30 ml) containing 270 ppm of NTA and oxamide to be purified (3 g) are charged into an autoclave as in example 1. The stirred mixture is heated to 120° C. for 3 hours and then cooled to room temperature. Upon centrifugation, washing with water (20 ml) and drying at 100° C., 2.9 g of oxamide are recovered. Atomic absorption analysis reveals 36 ppm of copper.

EXAMPLE 4

Distilled water (30 ml) and oxamide to be purified (3 g) are charged into an autoclave as in example 1. The mixture is heated at 120° C. under stirring for 3 hours then it is cooled to room temperature. Upon centrifugation and drying at 100° C., 2.5 g of oxamide containing 746 ppm of copper are recovered.

EXAMPLE 5

Water (30 ml) containing 270 ppm of EDTA disodium salt, and oxamide to be purified (3 g) are charged into an autoclave as in example 1. The mixture is heated to 120° C., under stirring, for 3 hours, and then cooled to room temperature. Upon centrifugation, washing with water (20 ml) and drying at 100° C., 2.9 g of oxamide containing 28 ppm of copper are recovered.

We claim:

1. A process for removing copper from a copper-containing oxamide, which comprises:

a) contacting the oxamide with an effective amount of an aqueous solution of a complexing agent which is capable of forming copper-containing water-soluble complexes and which imparts to the aqueous solution a pH in the range of 2 to 8, and b) removing purified oxamide from the solution of the copper-containing complex, and wherein the complexing agent comprises a secondary or tertiary nitrogen-containing organic compound having two or more carboxy groups, which are either free or partially salified.

2. The process as claimed in claim 1, wherein the complexing agent is selected from the group consisting of N,N'-1,2-ethandiylbis(N-(carboxymethyl)-glycine), N,N-bis(carboxymethyl)glycine, N,N-bis(2-(bis(carboxymethyl)amino)ethyl)glycine, N,N'-cyclohexandiylbis(N-(carboxymethyl)glycine), N,N'-(oxydi-2,1-ethandiyl)bis(N-(carboxymethyl)-glycine), N,N'-(thiodi-2,1-ethandiyl)bis(N-(carboxymethyl)glycine) and the corresponding derivatives partially salified with alkali or alkaline-earth metals.

3. The process as claimed in claim 1, wherein the concentration, by weight, of the complexing agent in the aqueous solution is between 0.01 and 10%.

4. The process as claimed in claim 3, wherein said concentration is between 0.2 and 6.0%.

5. The process as claimed in claim 1, wherein oxamide is contacted with the aqueous solution of the complexing agent at a temperature between 60° and 150° C.

6. The process as claimed in claim 5, wherein the temperature is between 100° and 125° C.

7. The process as claimed in claim 1, wherein the contacting time between the oxamide and the aqueous solution of the complexing agent is between 1 and 6 hours.

8. The process as claimed in claim 1, wherein the step of contacting oxamide with the aqueous solution of the complexing agent is repeated one or more times.

9. The process as claimed in claim 1, wherein the starting oxamide has a particle size between 300 and 3,000 mesh.

10. The process as claimed in claim 9, wherein said purified oxamide contains less than 25 ppm of copper.

11. The process as claimed in claim 1, wherein said copper-containing oxamide is contacted with said complexing agent by using a multiple-contact system in which oxamide is subjected to multiple contacts with aqueous solutions of the complexing agent having different extraction efficiencies.

* * * * *